(12) United States Patent
Bernard et al.

(10) Patent No.: US 6,596,753 B2
(45) Date of Patent: *Jul. 22, 2003

(54) COMPOUNDS OF THE INDOLECARBOXYLIC FAMILY AND USE THEREOF

(75) Inventors: Bruno Bernard, Neuilly-sur-Seine (FR); Catherine Gerst, Asnières (FR); Jean-Baptiste Galey, Aulnay-sous-Bois (FR); Maria Dalko, Gif-sur-Yvette (FR); Patrick Pichaud, Vélizy (FR)

(73) Assignee: Societe L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/176,674

(22) Filed: Jun. 24, 2002

(65) Prior Publication Data

US 2003/0050325 A1 Mar. 13, 2003

Related U.S. Application Data

(62) Division of application No. 09/297,636, filed as application No. PCT/FR98/01853 on Aug. 26, 1998, now Pat. No. 6,448,285.

(30) Foreign Application Priority Data

Sep. 5, 1997 (FR) .............................. 97 11076

(51) Int. Cl.$^7$ ..................... A61K 31/405; C07D 209/12
(52) U.S. Cl. ....................... 514/419; 548/491; 548/492
(58) Field of Search ............... 514/419; 548/491, 548/492

(56) References Cited

U.S. PATENT DOCUMENTS

| | | | |
|---|---|---|---|
| 4,956,174 A | 9/1990 | Lang et al. | |
| 5,449,403 A | 9/1995 | Andrean et al. | |
| 5,616,150 A | 4/1997 | Moeller et al. | |

FOREIGN PATENT DOCUMENTS

| | | |
|---|---|---|
| DE | 22 03 542 | 8/1973 |
| DE | 0 565 417 A1 | 10/1993 |
| WO | 94 22821 | 10/1994 |
| WO | 97 35572 | 10/1997 |
| WO | 99/07351 | 2/1999 |

OTHER PUBLICATIONS

J. Jap. Soc. Oleochem., (1997), 46(8), pp. 891–897.
Holt, Dennis A. et al, "Benzophenone– and Indolecarboxylic Acids: Potent Type–2 Specific Inhibitors of Human Steroid 5.alpha.–Reductase" J. Med. Chem. (1995), 38(1), 13–15, 1995, XP002068506, cited in the application.
Kita, Yasuyuki et al, "Total synthesis of discorhabdin C: a general aza spiro dienone formation from O–silylated phenol derivatives using a hypervalent iodine reagent" J. Am. Chem. Soc. (1992), 114(6), 2175–80, 1992, XP002068507, * p. 2176, scheme II *.

Chemical Abstracts, vol. 83, No. 7, Aug. 18, 1975, Columbus, Ohio, US; Abstract No. 58582, Nantka–Namirski, Pawel et al, "Derivatives of 2–carbethoxyindole. III. Products of amidation and alkylation of 5–benzyloxy–and 5–methoxy–2–carbethoxyindole" XP002068510, see abstract & Acta Pol. Pharm. (1974), 31(5), 569–76, 1974.

Chemical Abstracts, vol. 68, No. 5, Jan. 29, 1968, Columbis, Ohio, US, Abstract No. 21765, Keglevic, Dina et al, Synthesis of serotonin carbon–14 labeled in the ring (5–hydroxytryptamine–3–14C) XP002068511, see abstract & J. Labelled Compd. (1967), 3(2), 144–8 Coden: JLCAAI, 1967.

Chemical Abstracts, vol. 108, No. 1, Jan. 4, 1988, Columbus, Ohio, US; Abstract No. 5930, Partsvaniya, D.A. et al, "Indole derivatives. 128. Synthesis and properties of 5,6–and 4,5–(ethylenedioxy)indoles" XP002068512 * 2,3–dihydro–7H–1,4–dioxino'2,3–e indole–8–carboxylic acid (RN=111506–25–3) * & Khim. Geterotsikl. Soedin. (1986), (12), 1624–8, 1986.

Chemical Abstracts, vol. 92, No. 19, May 12, 1980, Columbus, Ohio, US; Abstract No. 163872, Suvorov, N.N. et al, "Some results of studies of synthesis methods and properties of isomeric pyrroloquinolines", XP002068513, see abstract & Tr.—Mosk. Khim.–Tekhnol. Inst. Im. D. I. Mendeleeva (1977), 94, 23–31, 1977.

Hosmane, R.S. et al, "Synthesis of benzeindole and benzgindole carboxaldehydes", J. Heterocycl. Chem. (1974), 99(1), 29–32, 1974, XP002068508, * composes X, XIV, XVI, XVIII * , see p. 29.

*Primary Examiner*—Taofiq Solola
(74) *Attorney, Agent, or Firm*—Burns, Doane, Swecker & Mathis, L.L.P.

(57) ABSTRACT

The invention relates to the use, as active principle, in a physiologically acceptable medium, in a composition, of an effective amount of at least one compound of the indolecarboxylic family, this compound or these compositions being intended to treat disorders associated with overactivity of 5α-reductase. These compounds or the compositions containing them are more particularly intended to treat androgen-dependent disorders such as, for example, seborrhoea and/or acne and/or hirsutism and/or androgenic alopecia. The invention also relates to novel compounds of the indolecarboxylic family and to compositions-containing them.

23 Claims, No Drawings

COMPOUNDS OF THE INDOLECARBOXYLIC FAMILY AND USE THEREOF

CROSS-REFERENCE TO RELATED APPLICATIONS

This application is a divisional of U.S. application Ser. No. 09/297,636, filed Jul. 26, 1999, now U.S. Pat. No. 6,448,285, incorporated by reference herein in its entirety and relied upon, which is a national stage filing under 35 U.S.C. §371 of International PCT Application No. PCT/FR98/01853, filed Aug. 26, 1998.

BACKGROUND OF THE INVENTION

1. Field of the Invention

The present invention relates to the use of an effective amount of at least one compound of the indolecarboxylic family for treating disorders associated with overactivity of 5α-reductase, and more particularly androgen-dependent disorders.

2. Background of the Related Art

Androgens are hormones defined as belonging to the steroid family which have a specific structure.

Androgens act at many sites in the human body and are similarly involved in a large number of disorders, among which mention may be made of prostate carcinomas, benign hyperplasia of the prostate, acne, hursutism, seborrhoea, androgenic alopecia, cheloids and adhesions, ovarian polycystic syndrome, premenstrual syndrome, lung cancer in man, precocious puberty and Fox-Fordyce disease.

Androgens are lipid substances which easily cross cell membranes. The mechanism of action of androgens takes place by interaction with a receptor which is specific to them: the androgen receptor.

Testosterone emerges as the major androgen. The metabolic routes for the androgens, in particular for testosterone, are nowadays well known.

One of the metabolic routes for testosterone is its conversion via 5α-reductase into dihydrotestosterone (DHT). Testosterone and DHT bind to the androgen receptor, but DHT has a much higher affinity for this receptor than testosterone. Furthermore, the DHT/receptor binding is much more stable than the testosterone/receptor binding.

Two isoforms of 5α-reductase have been isolated and cloned to date. Type 1 5α-reductase is mainly expressed in the skin and the various compartments of hair follicles, particularly in the keratinocytes of the epidermis and/or of the follicles, in the cells of the dermal papilla, the outer sheath of the hair follicles, the sebaceous glands and in the sweat glands.

Type 2 5α-reductase is itself expressed in the epididymis, the seminal vesicles, the prostate, foetal genital skin or alternatively the inner sheath of the hair follicles or in the fibroblasts of adult genital skin.

Since type 1 5α-reductase is mainly expressed in the skin and the various compartments of the hair follicles, the development of type 1 5α-reductase inhibitors represents an approach of choice for treating androgen-dependent disorders, whether they are manifested in the skin or in the hair follicles.

It has long been sought to develop 5α-reductase inhibitors as a treatment for androgen-associated disorders. Many compounds have been proposed in this conceptual vein. To date, two classes of inhibitor have been synthesized: steroidal inhibitors and non-steroidal inhibitors (see in this respect the article by Chen et al. "The 5α-reductase system and its inhibitors" (Dermatology, 1996, 193, 177–184)).

Among the steroidal inhibitors, mention may be made of 6-azasteroid derivatives and especially 4-azasteroid derivatives, including [17p-(N-tert-butylcarbamoyl)-4-aza-5α-androstan-1-en-3-one](finasteride), which is an inhibitor specific for the isotype 2, and 7β-methyl-4-azacholestan-3-one (MK-386), which is an inhibitor specific for the isotype 1. The drawback of steroidal inhibitors is that they have non-negligible side effects which make them problematic to use.

Among the non-steroidal inhibitors, mention may be made of certain benzoylaminophenoxybutanoic acid derivatives, benzoquinolines such as trans-8-chloro-4-methyl-1,2,3,4,4a,5,6,10b-octahydrobenzo[f]quinolin-3-one (LY 191704), 4-[3-([bis(4-isobutylphenyl)methylamino] benzoyl)-1H-indol-1-yl]butyric acid (FK143), polyunsaturated fatty acids, cations such as copper and zinc, and epicatechin derivatives. Similarly, indole derivatives have been described, such as, for example, in patent applications EP-458,207, EP-511,477, EP-600,084, EP-628,040, WO 91/13060, WO 93/02050, WO 93/02051, WO 93/05019, WO 93/16996, WO 94/27990, WO 95/05375, WO 95/23143, JP-07,304,736 and JP-07,188,164.

Relatively little has been described regarding the class of indolecarboxylic derivatives. Holt et al. (J. Med. Chem., 1995, 38, 13–15) have described molecules which have strong inhibitory activity with respect to type 2 5α-reductase.

SUMMARY AND DETAILED DESCRIPTION OF THE INVENTION

Thus, a first subject of the invention relates to the use, in a composition, of an effective amount of at least one compound corresponding to the general formula (I)

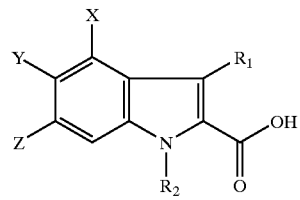

Formula (I)

in which X and Y, which may be identical or different,
represent a hydrogen atom or a radical —O—$CHR_3R_4$, in which $R_3$ is a hydrogen atom or an optionally substituted phenyl radical or alternatively a 5- or 6-membered heterocycle and $R_4$ is an optionally substituted phenyl radical or alternatively a 5- or 6-membered heterocycle, or $R_3$ and $R_4$ taken together form, with the carbon atom, a 5- or 6-membered ring or heterocycle;

or, taken together, form, with the 2 carbon atoms bearing them, a ring or a heterocycle containing 5 or 6 carbon atoms;

Z represents a hydrogen atom or a radical —O—$R_5$ in which $R_5$ is a $C_1$–$C_6$ alkyl radical or a $C_6$–$C_{12}$ aralkyl radical;

$R_1$ represents a hydrogen atom or a $C_1$–$C_6$ alkyl radical or a $C_6$–$C_{12}$ aralkyl radical which is optionally substituted;

$R_2$ represents a hydrogen atom or a $C_1$–$C_6$ alkyl radical or a radical —$CHR_3R_4$, in which $R_3$ and $R_4$ have the above definitions;

it being understood that when $R_2$ is a hydrogen atom or a methyl radical and X is a hydrogen atom, then Y must be other than an —O—$CH_2$ Phenyl radical and Z must be other than a hydrogen atom, and that when $R_2$ is a hydrogen atom or a methyl radical and X is a hydrogen atom, then Y must be other than a hydrogen atom and Z must be other than an —O—$CH_2$ Phenyl radical and that R, X, Y and Z cannot simultaneously be a hydrogen atom, the compound or the composition being intended to treat disorders associated with androgens and/or with overactivity of 5α-reductase.

The compounds of the invention corresponding to the formula (I) can be used, for example, to treat prostate carcinomas, benign hyperplasia of the prostate, acne, hirsutism, seborrhoea, androgenic alopecia, cheloids and adhesions, ovarian polycystic syndrome, premenstrual syndrome, lung cancer in man, precocious puberty and Fox-Fordyce disease.

Preferably, the compounds corresponding to formula (I) according to the invention can be used to induce and/or stimulate hair growth and/or to slow down hair loss and/or in the treatment of hyperseborrhoea and/or of acne.

Particularly, the invention relates to the use, in a composition, of an effective amount of at least one compound corresponding to the general formula (I) as defined above, this compound or the composition being intended to treat disorders associated with overactivity of 5α-reductase.

Thus, a subject of the invention is the use, in a composition, of an effective amount of at least one compound corresponding to the general formula (I) as defined above, this compound and/or the composition being intended to treat acne, hirsutism, seborrhoea, androgenic alopecia, cheloids and adhesions, prostate carcinomas, benign hyperplasia of the prostate, ovarian polycystic syndrome, premenstrual syndrome, lung cancer in man, precocious puberty and Fox-Fordyce disease.

Preferably, a subject of the invention is the use, in a composition, of an effective amount of at least one compound corresponding to the general formula (I) as defined above, this compound the composition being intended to induce and/or stimulate hair growth and/or to slow down hair loss and/or to treat hyperseborrhoea and/or acne.

Needless to say, the compounds corresponding to the formula (I) according to the invention can be used alone or as a mixture.

Among the compounds preferably used according to the invention, mention may be made of 4-benzyloxy-6-methoxy-1H-indole-2-carboxylic acid, 4-[3,5-bis(trifluoromethyl)benzyloxy]-6-methoxy-1H-indole-2-carboxylic acid, 5-benzyloxy-6-methoxy-1H-indole-2-carboxylic acid, 5-[3,5-bis(trifluoromethyl)benzyloxy]-6-methoxy-1H-indole-2-carboxylic acid, 5-(3,4,5-trimethoxybenzyloxy)-6-methoxy-1H-indole-2-carboxylic acid, 5,6-bis(benzyloxy)-3-methyl-1H-indole-2-carboxylic acid, 5,6-bis(benzyloxy)-1H-indole-2-carboxylic acid, 5-(4-methoxybenzyloxy)-6-methoxy-1H-indole-2-carboxylic acid, 5-(4-cyanobenzyloxy)-6-methoxy-1H-indole-2-carboxylic acid, 1-[3,5-bis(trifluoromethyl)benzyl]-5-[3,5-(trifluoromethyl)benzyloxy]-6-methoxy-1H-indole-2-carboxylic acid, 3H-benz[e]indole-2-carboxylic acid, 3-methyl-3H-benz[e]indole-2-carboxylic acid, 3-benzyl-3H-benz[e]indole-2-carboxylic acid, 3-[3,5-bis(trifluoromethyl)benzyl]-3H-benz[e]indole-2-carboxylic acid.

Among these compounds, the ones most particularly preferred are:

5-benzyloxy-6-methoxy-1H-indole-2-carboxylic acid,

5-[3,5-bis(trifluoromethyl)benzyloxy]-6-methoxy-1H-indole-2-carboxylic acid, 3H-benz[e]indole-2-carboxylic acid, 3-methyl-3H-benz[e]indole-2-carboxylic acid, 5,6-bis(benzyloxy)-1H-indole-2-carboxylic acid.

The amount of compounds of formula (I) which can be used according to the invention depends, needless to say, on the desired effect and can thus vary within a wide range.

In order to give an order of magnitude, the compound of formula (I) can be used according to the invention in an amount representing from 0.001% to 10% of the total weight of the composition and preferably in an amount representing from 0.01% to 5% of the total weight of the composition.

According to the invention, the compounds of formula (I) can be used in compositions for cosmetic or pharmaceutical use. Preferably, according to the invention, the compounds of formula (I) are used in compositions for cosmetic use.

In the treatment of hair loss, as in that of seborrhoea or acne, the cosmetic composition according to the invention is to be applied to the areas to be treated and is optionally left in contact for several hours and is optionally to be rinsed off. It is possible, for example, to apply the composition containing an effective amount of at least one compound as defined above, in the evening, keep this composition in contact throughout the night with the areas to be treated, and optionally rinse it off in the morning. These applications can be repeated daily for one or more months depending on the individual.

Thus, a second subject of the present invention is a cosmetic treatment process for the hair and/or the scalp and/or the skin, characterized in that it consists in applying to the hair and/or the scalp and/or the skin a cosmetic composition comprising an effective amount of at least one compound corresponding to formula (I), in leaving this composition in contact with the hair and/or the scalp and/or the skin, and in optionally rinsing it out.

The treatment process has the characteristics of a cosmetic process since it improves the beauty of the hair and/or the skin by giving them greater vigour and a better appearance.

Thus, the indolecarboxylic compounds have noteworthy activities which justify their use for treating disorders associated with androgens and/or with overactivity of 5α-reductase.

In this regard, after extensive studies, the Applicant has discovered novel indolecarboxylic derivatives which are specific inhibitors of type 1 or type 2 5α-reductase, or which can be considered as mixed inhibitors, i.e. compounds with pronounced inhibitory activity with regard to the two forms.

Thus, a third subject of the invention is an indolecarboxylic derivative corresponding to the general formula (I'):

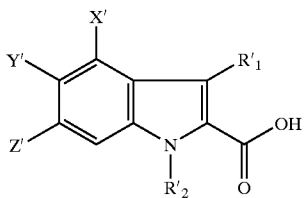

Formula (I')

in which X' and Y', which may be identical or different, represent a hydrogen atom or a radical —O—CHR$_{13}$R$_{14}$, in which R$_{13}$ is a hydrogen atom or an optionally substituted phenyl radical or alternatively a 5- or 6-membered heterocycle and R'$_4$ is an optionally substituted phenyl radical or alternatively a 5- or 6-membered heterocycle, or R$_{13}$ and R$_{14}$ taken together form, with the carbon atom, a 5- or 6-membered ring or heterocycle;

or, taken together, form, with the 2 carbon atoms bearing them, a ring or a heterocycle containing 5 or 6 carbon atoms;

Z represents a hydrogen atom or a radical —O—R$_{15}$ in which R$_{15}$ is a C$_1$–C$_6$ alkyl radical or a C$_6$–C$_{12}$ aralkyl radical;

R'$_1$ represents a hydrogen atom or a C$_1$–C$_6$ alkyl radical or a C$_6$–C$_{12}$ aralkyl radical, which is optionally substituted;

R'$_2$ represents a hydrogen atom or a C$_1$–C$_6$ alkyl radical or a radical —CHR$_{13}$R$_{14}$, in which R$_{13}$ and R$_{14}$ have the above definitions;

or the esters thereof or the optical isomers thereof, alone or as a mixture in all proportions, the acylated forms thereof or alternatively the pharmaceutically acceptable salts thereof, it being understood:
that when X' is a hydrogen atom and Y' is a radical —OCHR$_{13}$R$_{14}$ in which CHR$_{13}$R$_{14}$ represents an aralkyl radical, then Z' cannot be a radical —OR$_{15}$, and that when X' is an —O—CH$_2$Phenyl radical, then Y' and Z' must not be a hydrogen atom.

According to the invention, the term "heterocycle" preferably refers to a ring optionally containing one or more nitrogen and/or oxygen atoms, and particularly pyridine, imidazole, tetrahydrofuran or furan. A heterocycle which is particularly preferred according to the invention is pyridine.

According to the invention, the term "C$_1$–C$_6$ alkyl radical" preferably refers to linear or branched, saturated or unsaturated alkyl radicals containing from 1 to 6 carbon atoms.

Preferably, according to the invention, the alkyl radical is C$_1$–C$_4$ and is chosen from methyl, ethyl, propyl, isopropyl, butyl, isobutyl and tert-butyl radicals and more particularly methyl and ethyl radicals.

According to the invention, the term "C$_6$–C$_{12}$ aralkyl radical" preferably refers to alkylaryl radicals containing from 6 to 12 carbon atoms, in which definition the term "aryl" is understood as a 5- or 6-membered aromatic ring or a 5- or 6-membered aromatic heterocycle. Preferably, according to the invention, the aralkyl radical is C$_7$–C$_{10}$. An aralkyl radical which is particularly preferred according to the invention is the benzyl radical.

According to the invention, the term "substituted phenyl radical" preferably refers to a phenyl radical substituted with a cyano (—CN) group, a trifluoromethyl (—CF$_3$) group, a methoxy (—O—CH$_3$) radical or a halogen atom. The halogen atom can be chosen from chlorine, bromine, fluorine and iodine. A substituted phenyl radical which is particularly preferred according to the invention is the phenyl radical substituted with a trifluoromethyl (—CF$_3$) group.

According to one specific embodiment of the invention, R'$_1$ is preferably a methyl radical.

According to another embodiment of the invention, R'$_1$ is a benzyl radical.

According to one specific embodiment of the invention, R'$_2$ is preferably a methyl radical.

According to another embodiment of the invention, R'$_2$ is a 3,5-bis(trifluoromethyl)benzyl radical.

When R'$_3$ is a substituted phenyl radical, R'$_3$ is preferably a 3,5-bis(trifluoromethyl)phenyl radical.

When R'$_3$ is a heterocycle, R'$_3$ is preferably a pyridine.

When R'$_4$ is a substituted phenyl radical, R'$_4$ is preferably a 3,5-bis(trifluoromethyl)phenyl radical.

When R'$_4$ is a heterocycle, R'$_4$ is preferably a pyridine.

According to one specific embodiment of the invention, R'$_5$ is preferably a methyl radical.

According to another embodiment of the invention, R'$_5$ is an ethyl radical.

As compounds of formula (I'), mention may be made of:
4-benzyloxy-6-methoxy-1H-indole-2-carboxylic acid,
4-[3,5-bis(trifluoromethyl)benzyloxy]-6-methoxy-1H-indole-2-carboxylic acid,
5-[3,5-bis(trifluoromethyl)benzyloxy]-6-methoxy-1H-indole-2-carboxylic acid,
5-(3,4,5-trimethoxybenzyloxy)-6-methoxy-1H-indole-2-carboxylic acid,
5-(4-methoxybenzyloxy)-6-methoxy-1H-indole-2-carboxylic acid,
5-(4-cyanobenzyloxy)-6-methoxy-1H-indole-2-carboxylic acid,
1-[3,5-bis(trifluoromethyl)benzyl]-5-[3,5-(trifluoromethyl)benzyloxy]-6-methoxy-1H-indole-2-carboxylic acid,
3H-benz[e]indole-2-carboxylic acid,
3-methyl-3H-benz[e]indole-2-carboxylic acid,
3-benzyl-3H-benz[e]indole-2-carboxylic acid,
3-[3,5-bis(trifluoromethyl)benzyl]-3H-benz[e]indole-2-carboxylic acid.

Among these compounds, the ones most particularly preferred are:
5-[3,5-bis(trifluoromethyl)benzyloxy]-6-methoxy-1H-indole-2-carboxylic acid,
3H-benz[e]indole-2-carboxylic acid,
3-methyl-3H-benz[e]indole-2-carboxylic acid.

A fourth subject of the invention relates to cosmetic or pharmaceutical compositions, in particular dermatological compositions, which comprise at least one of the compounds corresponding to formula (I') defined above.

Needless to say, the compositions according to the invention can comprise the compounds of formula (I') alone or as mixtures in all proportions.

The amount of compounds of formula (I') contained in the compositions of the invention depends, needless to say, on the desired effect and can thus vary within a wide range.

In order to give an order of magnitude, the composition of the invention can contain at least one compound of formula (I') in an amount representing from 0.001% to 10% of the total weight of the composition, and preferably in an amount representing from 0.01% to 5% of the total weight of the composition.

The composition of the invention can be a composition for cosmetic or pharmaceutical use. Preferably, according to the invention, the composition of the invention can be a composition for cosmetic use.

The composition can be ingested, injected or applied onto the skin (on any area of body skin), the hair, the nails or mucous membranes (buccal, jugal, gingival, genital or conjunctival membranes). Depending on the mode of administration, the composition according to the invention can be in any pharmaceutical form normally used.

For topical application to the skin, the composition can be, in particular, in the form of an aqueous or oily solution or of a dispersion of the lotion or serum type, of emulsions of liquid or semi-liquid consistency of the milk type, obtained by dispersing a fatty phase in an aqueous phase (O/W) or, conversely, (W/O), or of suspensions or emulsions of soft consistency of the aqueous or anhydrous cream or gel type, or alternatively of microcapsules or microparticles, or of vesicular dispersions of ionic and/or nonionic type. These compositions are prepared according to the usual methods.

They can also be used for the hair in the form of aqueous, alcoholic or aqueous-alcoholic solutions, or in the form of creams, gels, emulsions or mousses, or alternatively in the form of aerosol compositions also comprising a propellant under pressure.

The composition according to the invention can also be a hair care composition, and in particular a shampoo, a hairsetting lotion, a treating lotion, a styling cream or gel, a dye composition (in particular an oxidation dye composition) optionally in the form of colouring shampoos, restructuring lotions for the hair, a permanent-waving composition (in particular a composition for the first stage of a permanent-waving operation), a lotion or gel for preventing hair loss, an antiparasitic shampoo, etc.

For injection, the composition can be in the form of an aqueous or oily lotion or in the form of a serum. For the eyes, it can be in the form of drops, and for ingestion, it can be in the form of capsules, granules, syrups or tablets.

The amounts of the various constituents in the compositions according to the invention are those conventionally used in the fields considered.

The compositions according to the invention can also consist of solid preparations constituting cleansing soaps or bars.

The compositions can also be packaged in the form of an aerosol composition also comprising a propellant under pressure.

When the composition is an emulsion, the proportion of the fatty phase can range from 5% to 80% by weight, and preferably from 5% to 50% by weight, relative to the total weight of the composition. The oils, the waxes, the emulsifiers and the co-emulsifiers used in the composition in emulsion form are chosen from those conventionally used in the cosmetics field. The emulsifier and the co-emulsifier are present in the composition in a proportion ranging from 0.3% to 30% by weight, and preferably from 0.5 to 20% by weight, relative to the total weight of the composition. The emulsion can also contain lipid vesicles.

When the composition is an oily solution or gel, the fatty phase can represent more than 90% of the total weight of the composition.

In a known manner, the cosmetic composition can also contain adjuvants that are common in the cosmetics field, such as hydrophilic or lipophilic gelling agents, hydrophilic or lipophilic additives, preserving agents, antioxidants, solvents, fragrances, fillers, screening agents, odour absorbers and dyestuffs. The amounts of these various adjuvants are those conventionally used in the cosmetics field and, for example, from 0.01% to 10% of the total weight of the composition. Depending on their nature, these adjuvants can be introduced into the fatty phase, into the aqueous phase and/or into the lipid spherules.

As oils or waxes which can be used in the invention, mention may be made of mineral oils (liquid petroleum jelly), plant oils (liquid fraction of karite butter, sunflower oil), animal oils (perhydrosqualene), synthetic oils (purcellin oil), silicone oils or waxes (cyclomethicone), fluoro oils (perfluoropolyethers), beeswax, carnauba wax or paraffin wax. Fatty alcohols and fatty acids (stearic acid) can be added to these oils.

As emulsifiers which can be used in the invention, mention may be made, for example, of glyceryl stearate, polysorbate-60 and the mixture of PEG-6/PEG-32/glycol stearate sold under the name Tefose® 63 by the company Gattefosse.

As solvents which can be used in the invention, mention may be made of lower alcohols, in particular ethanol and isopropanol, and propylene glycol.

As hydrophilic gelling agents which can be used in the invention, mention may be made of carboxyvinyl polymers (carbomer), acrylic copolymers such as acrylate/alkyl acrylate copolymers, polyacrylamides, polysaccharides such as hydroxypropyl cellulose, natural gums and clays, and, as lipophilic gelling agents, mention may be made of modified clays such as bentones, metal salts of fatty acids such as aluminium stearates, and hydrophobic silica, ethyl cellulose and polyethylene.

The composition can contain other hydrophilic active agents, such as proteins or protein hydrolysates, amino acids, polyols, urea, allantoin, sugars and sugar derivatives, water-soluble vitamins, plant extracts and hydroxy acids.

Lipophilic active agents which may be used are retinol (vitamin A) and its derivatives, tocopherol (vitamin E) and its derivatives, essential fatty acids, ceramides, essential oils and salicyclic acid and its derivatives.

According to the invention, the composition can combine at least one compound of formula (I) with other active agents. Among these active agents, mention may be made, for example, of:

agents for improving the activity with regard to the regrowth of the hair and/or with regard to slowing down hair loss, and which have already been described for this activity, such as, for example, nicotinic acid esters including, in particular, tocopheryl nicotinate, benzyl nicotinate and $C_1-C_6$ alkyl nicotinates such as methyl or hexyl nicotinates, pyrimidine derivatives, for instance 2,4-diamino-6-piperidinopyrimidine 3-oxide or "Minoxidil" described in U.S. Pat. Nos. 4,139,619 and 4,596,812, and agents for promoting regrowth of the hair, for instance those described by the Applicant in the European patent application published under the number 0,648,488;

agents for reducing skin differentiation and/or proliferation and/or pigmentation, such as retinoic acid and its isomers, retinol and its esters, vitamin D and its derivatives, oestrogens such as oestradiol, kojic acid or hydroquinone;

antibacterial agents such as clindamycin phosphate, erythromycin or antibiotics of the tetracycline class;

antiparasitic agents, in particular metronidazole, crotamiton or pyrethroids;

antifungal agents, in particular the compounds belonging to the imidazole class, such as econazole, ketoconazole or miconazole or their salts, polyene compounds, such as amphotericin B, compounds of the allylamine family, such as terbinafine, or alternatively octopirox;

antiviral agents such as acyclovir;

steroidal anti-inflammatory agents, such as hydrocortisone, betamethasone valerate or clobetasol propionate, or non-steroidal anti-inflammatory agents such as, for example, ibuprofen and its salts, diclofenac and its salts, acetylsalicylic acid, acetaminophen or glycyrrhizic acid;

anaesthetics such as lidocaine hydrochloride and its derivatives;

anti-pruriginous agents such as thenaldine, trimeprazine or cyproheptadine;

keratolytic agents such as α- and β-hydroxycarboxylic or β-ketocarboxylic acids, their salts, amides or esters and more particularly hydroxy acids such as glycolic acid, lactic acid, salicylic acid, citric acid and fruit acids in general, and 5-(n-octanoyl)salicylic acid;

anti-free-radical agents, such as α-tocopherol or its esters, superoxide dismutases, certain metal-chelating agents or ascorbic acid and its esters;

antiseborrhoeic agents such as progesterone;

antidandruff agents such as octopirox or zinc pyrithione;

anti-acne agents such as retinoic acid or benzoyl peroxide; extracts of plant or bacterial origin.

Other compounds can also be added to the above list, namely, for example, diazoxide, spiroxazone, phospholipids such as lecithin, linoleic acid, linolenic acid, salicylic acid and its derivatives described in French patent FR 2,581,542, for instance salicylic acid derivatives bearing an alkanoyl group containing from 2 to 12 carbon atoms in position 5 of the benzene ring, hydroxycarboxylic or ketocarboxylic acids and their esters, lactones and their corresponding salts, anthralin, carotenoids, eicosatetraenoic acid and eicosatrienoic acid or their esters and amides, vitamin D and its derivatives, and extracts of plant or bacterial origin.

Thus, according to one specific mode, the composition according to the invention also comprises at least one agent chosen from antibacterial agents, antiparasitic agents, antifungal agents, antiviral agents, anti-inflammatory agents, anti-pruriginous agents, anaesthetics, keratolytic agents, anti-free-radical agents, anti-seborrhoeic agents, antidandruff agents, anti-acne agents and/or agents for reducing skin differentiation and/or proliferation and/or pigmentation, and extracts of plant or bacterial origin.

It can also be envisaged for the composition comprising at least one compound as defined above to be in liposomal form, as described in particular in patent application WO 94/22468 filed on Oct. 13, 1994 by the company Anti Cancer Inc. Thus, the compound encapsulated in the liposomes can be delivered selectively to the hair follicles.

When the composition according to the invention is a pharmaceutical composition, it can be administered parentally, enterally or topically. Preferably, the pharmaceutical composition is administered topically.

A fifth subject of the invention relates to the use, as a medicinal product, of the compounds of general formula (I).

The compounds of the invention can be synthesized by entirely conventional processes generally used in organic synthesis.

Detailed examples of these syntheses are furthermore given in the examples.

However, as an example and in very general terms, in order to obtain a compound of the invention substituted in positions 4 and 6, 2-hydroxy-4-alkoxybenzaldehyde of formula

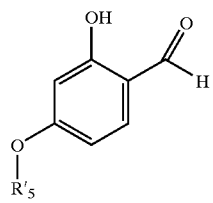

is reacted, in a first step, with a bromide of formula

in which R represents a hydrogen atom or a radical O—CHR'$_3$R'$_4$ as defined above, and R'$_5$ is as defined above, in the presence of anhydrous tetrahydrofuran (THF), of sodium hydride at 60% in oil and of tetrabutylammonium iodide.

After incubation for 6 hours at room temperature, the compound obtained is purified by chromatography on silica gel.

The term "room temperature" refers to a temperature of between 18° C. and 35° C., preferably of between 20° C. and 30° C.

In a second step, the compound obtained in the first step is reacted in the presence of sodium methoxide and ethyl azidoacetate in the presence of methanol for 20 hours at room temperature.

The compound thus obtained is purified by chromatography on silica gel or by recrystallization.

In a third step, the compound obtained in the second step is reacted in the presence of toluene, at reflux for one and a half hours. The compound thus obtained is purified by precipitation.

In a fourth step, the compound obtained in the third step is reacted in the presence of methanol, acetone and sodium hydroxide for 4 hours. The compound thus obtained is purified by precipitation.

Similarly, as an example and in very general terms, in order to obtain a compound of the invention substituted in positions 5 and 6, the 3-aralkoxy-4-alkoxybenzaldehyde of formula

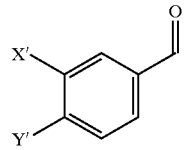

in which X' and Y' are defined as above, is nitrated, in a first step, with nitric acid at room temperature, for a period of between 2 h and 12 h.

The compound obtained is isolated by filtration.

In a second step, the compound obtained in the 1st step is reacted in the presence of calcium carbonate ($K_2CO_3$) with triethyl phosphonate in a mixture of ethanol and dimethoxyethane at 80° C. for a period of between 10 and 20 hours. The compound obtained is purified by chromatography on a column of silica.

In a third step, the compound obtained in the 2nd step is reacted with triethyl phosphate at reflux for a period of between 2 and 6 hours. The compound obtained is purified by chromatography on a column of silica.

In a fourth step, the compound obtained in the 3rd step is saponified with sodium hydroxide in an acetone/methanol mixture for a period of between 1 and 6 hours at a temperature of between 20° C. and 40° C. The compound obtained is purified by crystallization.

In order to obtain a compound for which X' and Y' form a ring or a heterocycle, a bicyclic aromatic aldehyde is reacted, in a first step, in the presence of sodium methoxide, ethyl azidoacetate and methanol.

After incubation for several hours at room temperature, the compound obtained is purified by chromatography on a column of silica.

In a second step, the compound obtained in the first step is reacted in the presence of refluxing toluene for several hours. The compound thus obtained is purified by recrystallization.

In a third step, the compound obtained in the second step is reacted in the presence of methanol, acetone and sodium hydroxide for 4 hours.

The compound thus obtained is purified by recrystallization.

For the preparation of compounds in which $R'_2$ is not a hydrogen atom, the compound obtained in the second step is placed in contact with an alkyl halide for 30 minutes at room temperature. The compound thus obtained is then reacted in the presence of acetone and sodium hydroxide for 1 hour at room temperature. The compound thus obtained is purified by recrystallization.

The indole carboxylic derivatives have inhibitory activities on 5α-reductase which it was possible to demonstrate by means of a screening test based on the in vitro expression of the isoforms 1 or 2 of 5α-reductase.

The details of these tests and the results obtained are given in the examples.

Examples, which cannot in any way limit the scope of the invention, will now be given for illustrative purposes.

EXAMPLE 1

Synthesis of 4-benzyloxy-6-methoxy-1H-indole-2-carboxylic acid a) Synthesis of 2-benzyloxy-4-methoxy-benzaldehyde of formula:

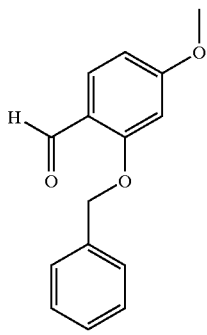

1 g of 2-hydroxy-4-methoxybenzaldehyde is dissolved in 15 ml of anhydrous tetrahydrofuran (THF) in a reactor. The mixture is cooled to 4° C. 1.3 equivalents of sodium hydride (NaH) at 60% in oil are added. The mixture is left to react for 30 minutes to form the alkoxide. 1.3 equivalents of benzyl bromide and 90 mg of tetrabutylammonium iodide are then added. The mixture is left to react for 6 hours at room temperature.

After reaction for 6 h, 50 ml of saturated sodium bicarbonate (NaHCO$_3$) solution are added. The mixture is washed twice with 50 ml of isopropyl ether. The organic phases are dried over sodium sulphate and evaporated under vacuum, and the compound obtained is purified on silica gel using dichloromethane as eluent. The mass recovered is 1.1 g, which corresponds to a yield of 69%.

b) Synthesis of Methyl 2-azido-3-(2-benzyloxy-4-methoxyphenyl)acrylate of formula:

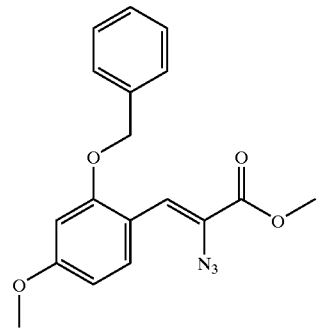

2 equivalents of sodium methoxide powder are introduced into 10 ml of methanol in a thoroughly dry three-necked flask, the whole system being under argon. 1.1 g of 2-benzyloxy-4-methoxybenzaldehyde, predissolved in 2 ml of methanol, are then added.

The mixture is cooled to −10° C. 5 equivalents of ethyl azidoacetate are dissolved in 5 ml of methanol and are added slowly to the 2-benzyloxy-4-methoxybenzaldehyde solution. After returning to room temperature, this mixture is left to react for 20 hours. The medium is diluted with 100 ml of dichloromethane and is washed twice with 50 ml of water. The organic phases are dried over sodium sulphate and evaporated under vacuum, and the compound obtained is purified on silica gel using heptane as eluent (gradient of ethyl acetate (EtOAc) up to 10%).

The mass recovered is 0.25 g, which corresponds to a yield of 15%.

c) Synthesis of Methyl 4-benzyloxy-6-methoxy-1H-indole-2-carboxylate of formula:

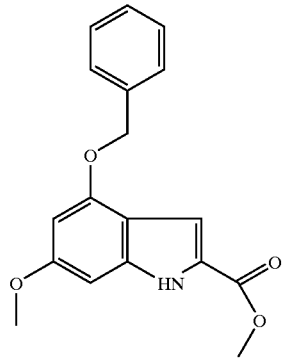

0.25 g of methyl 2-azido-3-(2-benzyloxy-4-methoxyphenyl)acrylate is dissolved in 10 ml of toluene. This solution is brought to reflux. After 1 h 30, the medium is concentrated to dryness under vacuum and the solid obtained is washed with 20 ml of heptane. A solid is obtained. The recovered mass is 0.11 g, which corresponds to a yield of 50%.

d) Synthesis of 4-benzyloxy-6-methoxy-1H-indole-2-carboxylic Acid of formula:

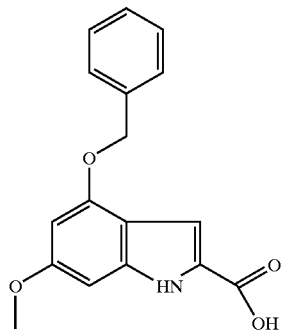

0.11 g of methyl 4-benzyloxy-6-methoxy-1H-indole-2-carboxylate is dissolved in 3 ml of acetone and 2 ml of methanol. 6 ml of 1N sodium hydroxide are then added. This mixture is left to react for 4 hours at room temperature. The medium is concentrated on a rotary evaporator and diluted with 20 ml of water. The resulting mixture is acidified to pH=2 with concentrated hydrochloric acid. A light brown solid is obtained. The recovered mass is 700 mg, which corresponds to a yield of 67%.

The $^1$H NMR analyses (200 MHz; CDCl$_3$), δ in ppm, gave the following results:

3.66 (3H; s), 5.0 (2H; s), 6.1 (1H; s), 6.27 (1H; s), 7.25 (6H; m), 8.66 (1H; s).

The structure of the compound obtained is in accordance with the expected structure.

EXAMPLE 2

Synthesis of 4-[3,5-bis(trifluoromethyl)benzyloxy]-6-methoxy-1H-indole-2-carboxylic acid:

a) Synthesis of 2-[3,5-bis(trifluoromethyl)benzyloxy]-4-methoxybenzaldehyde of formula:

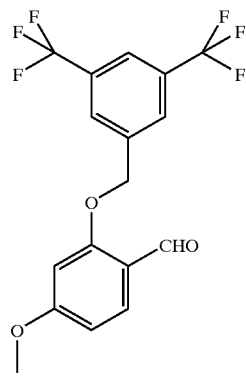

1.1 equivalents of sodium hydride (NaH) as a dispersion in oil are weighed out into a reactor. 20 ml of anhydrous dimethylformamide (DMF) are added. 0.95 equivalent of 2-hydroxy-4-methoxybenzaldehyde is then added to form the alkoxide. This mixture is left for 30 minutes at room temperature.

4.2 g of 3,5-bis(trifluoromethyl)benzyl bromide are added. The mixture is left to react for 1 h 30 at room temperature. 25 ml of saturated sodium bicarbonate (NaHCO$_3$) solution are added and this mixture is extracted twice with 20 ml of dichloromethane. The organic phases are dried over sodium sulphate and concentrated under vacuum to give a slightly pink oil. This oil is taken up in 15 μl of heptane and then in 20 ml of isopropyl ether. 3.6 g of an off-white solid are obtained, which corresponds to a yield of 74%.

b) Synthesis of Methyl 2-azido-2-{2-[3,5-bis(trifluoromethyl)benzyloxy]-4-methoxyphenyl}acrylate of formula:

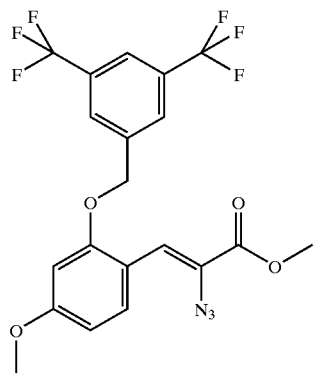

1 g of sodium methoxide powder is weighed out into a rigorously oven-dried reactor. 10 ml of methanol are added, followed by 3.5 g of 2-[3,5-bis(trifluoromethyl)benzyloxy]-4-methoxybenzaldehyde, predissolved in 5 ml of methanol. This mixture is cooled to 0° C.

4 equivalents of ethyl azidoacetate are dissolved in 5 ml of methanol and are then added to the above medium. After returning to room temperature, this mixture is left to react for 30 hours.

The medium is diluted with 20 ml of dichloromethane and is washed twice with 50 ml of water. The organic phase is dried over sodium sulphate. This solution is concentrated to dryness under vacuum and the oil obtained is purified on a column of silica using dichloromethane as eluent and with a methanol gradient (up to 2%). The recovered mass is 700 mg, which corresponds to a yield of 12%.

c) Synthesis of Methyl 4-[3,5-bis(trifluoromethyl)benzyloxy]-6-methoxy-1H-indole-2-carboxylate of formula:

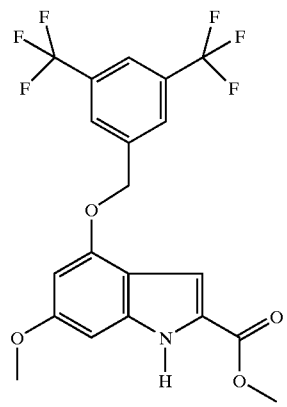

700 mg of methyl 2-azido-3-{2-[3,5-bis(trifluoromethyl)benzyloxy]-4-methoxyphenyl}acrylate are dissolved in 25 ml of toluene. This solution is refluxed for 3 hours. The medium is concentrated to dryness under vacuum. A pale yellow solid is obtained. This solid is taken up in 10 ml of isopropyl ether. The recovered mass is 460 mg, which corresponds to a yield of 83%.

d) Synthesis of 4-[3,5-bis(trifluoromethyl)benzyloxy]-6-methoxy-1H-indole-2-carboxylic Acid of formula:

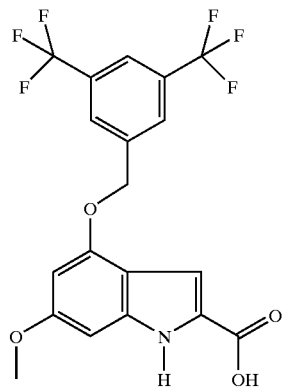

450 mg of methyl 4-[3,5-bis(trifluoromethyl)benzyloxy]-6-methoxy-1H-indole-2-carboxylate are dissolved in 15 ml of acetone, followed by addition of 15 ml of 1N sodium hydroxide. The mixture is left stirring for 4 hours at room temperature. The acetone is evaporated off under vacuum. The medium is diluted with 10 ml of water and is neutralised to pH=7 with concentrated hydrochloric acid. 300 mg of a white solid are obtained, which corresponds to a yield of 69%.

The $^1$H NMR analyses (200 MHz; DMSO), δ in ppm, gave the following results:

3.75 (3H; s), 5.42 (2H; s), 6.28 (1H; s), 6.51 (1H; s), 6.95 (1H; s), 8.1 (1H; s), 8.2 (2H; s), 11.5 (1H; s).

The structure of the compound obtained is in accordance with the expected structure.

EXAMPLE 3

Synthesis of 5-[3,5-bis(trifluoromethyl)benzyloxy]-6-methoxy-1H-indole-2-carboxylic Acid:

a) Synthesis of Ethyl 5-hydroxy-6-methoxy-1H-indole-2-carboxylate of formula:

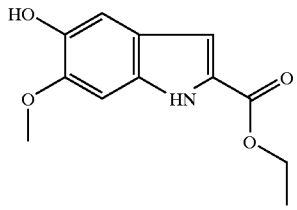

4.8 g of ethyl 5-benzyloxy-6-methoxy-1H-indole-2-carboxylate are dissolved in 150 ml of ethyl acetate (EtOAc) and 30 ml of ethanol. 4.8 g of activated palladium on charcoal (10%) are added and debenzylation is carried out under 5 bar of hydrogen for 2 h 30. The catalyst is filtered off through Celite and the medium is concentrated to dryness under vacuum. A pale grey solid is obtained.

The recovered mass is 2.55 g, which corresponds to a yield of 72%.

b) Synthesis of Ethyl 5-[3,5-bis(trifluoromethyl)benzyloxy]-6-methoxy-1H-indole-2-carboxylate

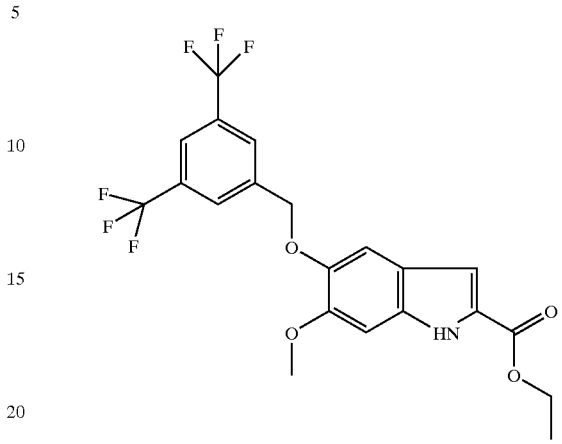

1.1 equivalents of sodium hydride (NaH) and 5 ml of anhydrous dimethylformamide (DMF) are introduced, under argon, into a reactor which has been dried in an oven beforehand. 0.3 g of ethyl 5-hydroxy-6-methoxy-1H-indole-2-carboxylate is then added at +3° C. and the mixture is left to react for 30 min at this temperature in order to form the alkoxide.

1.05 equivalents of 3,5-bis(trifluoromethyl)benzyl bromide are then added, still at +3° C. The mixture is left to react for 1 h 30 at this temperature. 25 ml of saturated sodium bicarbonate (NaHCO$_3$) solution are added with stirring for 1 hour. The mixture is washed twice with 50 ml of dichloromethane. The organic phases are dried over sodium sulphate and concentrated to dryness under vacuum. The residue obtained is purified on a column of silica using dichloromethane as solvent.

The recovered mass is 220 mg, which corresponds to a yield of 37%.

c) Synthesis of 5-[3,5-bis(trifluoromethyl)benzyloxy]-6-methoxy-1H-indole-2-carboxylic acid of formula:

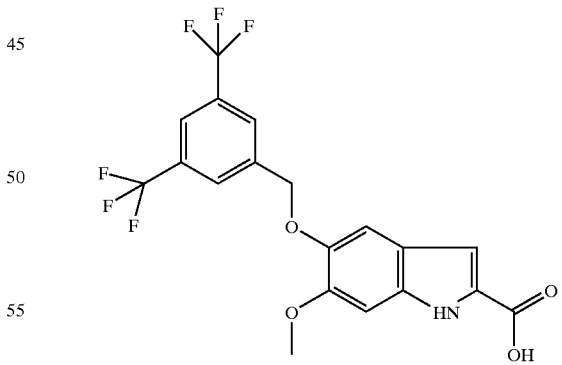

220 mg of ethyl 5-[3,5-bis(trifluoromethyl)benzyloxy]-6-methoxy-1H-indole-2-carboxylate are dissolved in 10 ml of acetone and 5 ml of methanol. 15 ml of 1N sodium hydroxide are added and the mixture is left to react for 3 hours at 30° C. The solvents are evaporated off under vacuum and the residue is then diluted with 5 ml of water. This mixture is acidified to pH=2 with concentrated hydrochloric acid. A precipitated is obtained, which is washed with water. The solid is taken up, while still wet, in 50 ml of refluxing pentane for 1 hour. The mixture is filtered under vacuum and 70 mg of solid are obtained, for a yield of 34%.

The $^1$H NMR analyses (200 MHz; DMSO), δ in ppm, gave the following results:

3.81 (3H; s), 5.27 (3H; s), 5.27 (2H; s), 6.91 (1H; s), 6.95 (1H; s),-7.24 (1H; s), 8.08 (1H; s), 8.17 (2H; s), 11.53 (1H; s), 12.65 (1H; s).

The structure of the compound obtained is in accordance with the expected structure.

| Elemental analysis | | | | |
| --- | --- | --- | --- | --- |
| | C in % | H in % | N in % | F in % |
| Theory | 52.67 | 3.02 | 3.23 | 26.31 |
| Found | 52.09 | 3.11 | 3.11 | 26.44 |

EXAMPLE 4

Synthesis of 5-(3,4,5-trimethoxybenzyloxy)-6-methoxy-1H-indole-2-carboxylic acid:

a) Synthesis of Ethyl 5-(3,4,5-trimethoxybenzyloxy)-6-methoxy-1H-indole-2-carboxylate of formula:

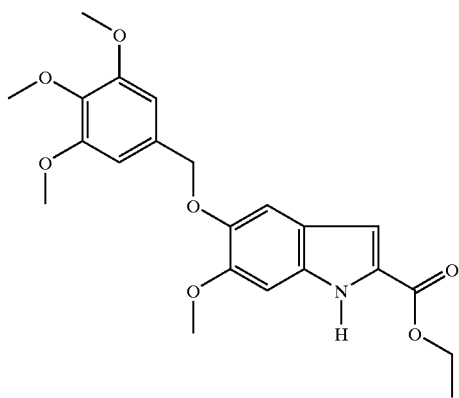

1.1 equivalents of sodium hydride (NaH) and 5 ml of anhydrous dimethylformamide (DMF) are introduced, under argon, into a reactor which has been dried beforehand in an oven. 0.3 g of ethyl 5-hydroxy-6-methoxy-1H-indole-2-carboxylate is then added at +3° C. and the mixture is left to react for 30 minutes at this temperature in order to form the alkoxide. 1.05 equivalents of 3,4,5-trimethoxybenzyl chloride are then added, still at +3° C. The mixture is left to react for 1 h 30 at this temperature. 10 mol % of tetrabutylammonium iodide is added and the mixture is left to react for a further 2 hours. 25 ml of saturated sodium bicarbonate (NaHCO$_3$) solution are then added with stirring for 1 hour. The mixture is washed twice with 50 ml of dichloromethane. The organic phases are dried over sodium sulphate and concentrated to dryness under vacuum. The residue obtained is purified on a column of silica using dichloromethane as solvent.

The recovered mass is 200 mg, which corresponds to a yield of 38%.

b) Synthesis of 5-(3,4,5-trimethoxybenzyloxy)-6-methoxy-1H-indole-2-carboxylic Acid of formula:

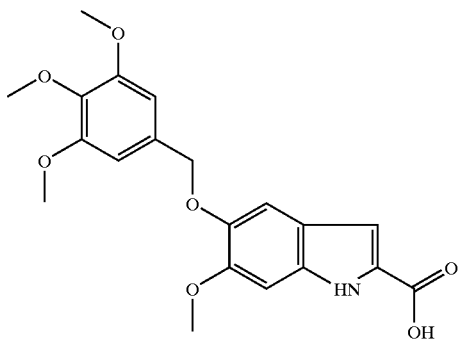

180 mg of methyl 5-(3,4,5-trimethoxybenzyloxy)-6-methoxy-1H-indole-2-carboxylate are dissolved in 15 ml of acetone and 3 ml of methanol. 15 ml of 1N sodium hydroxide are added and the mixture is left to react for 2 hours at 30° C. The solvents are evaporated off under vacuum and the residual aqueous phase is acidified to pH 2 with concentrated hydrochloric acid. A solid is obtained, which is purified by taking it up in ethyl acetate at room temperature.

The recovered mass is 35 mg, which corresponds to a yield of 21%.

The $^1$H NMR analyses (200 MHz; CDCl$_3$), δ in ppm, gave the following results:

3.6 (3H; s), 3.85 (9H; s), 4.95 (2H; s), 6.7 (1H; s), 6.8 (2H; s), 6.9 (1H; s), 7.5 (1H; s), 11.05 (1H; bs).

The structure of the compound obtained is in accordance with the expected structure.

EXAMPLE 5

Synthesis of 5-(4-methoxybenzyloxy)-6-methoxy-1H-indole-2-carboxylic acid:

a) Synthesis of Ethyl 5-(4-methoxybenzyloxy)-6-methoxy-1H-indole-2-carboxylate of formula:

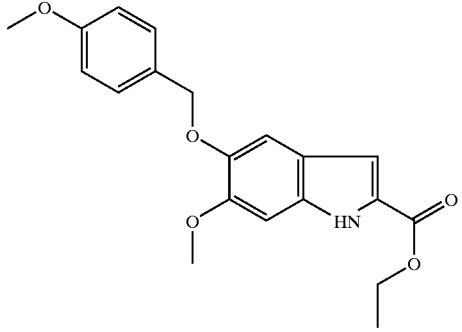

1.1 equivalents of sodium hydride (NaH) and 5 ml of anhydrous dimethylformamide (DMF) are introduced, under argon, into a reactor which has been dried beforehand in an oven. 0.4 g of ethyl 5-hydroxy-6-methoxy-1H-indole-2-carboxylate is then added at 0° C. and the mixture is left to react for 30 minutes at this temperature, in order to form the alkoxide. 1.1 equivalents of 4-methoxybenzyl chloride and 10 mol % of tetrabutylammonium iodide are then added. The mixture is left to react until it has returned to room temperature. The reaction is complete after 24 hours. 50 ml of saturated sodium bicarbonate (NaHCO$_3$) solution are then added and this mixture is extracted with twice 50 ml of dichloromethane. The organic phase is dried over sodium sulphate and concentrated to dryness under vacuum, and the residue obtained is purified on a column of silica using dichloromethane as eluent. The recovered mass is 200 mg, which corresponds to a yield of 32% b) Synthesis of 5-(4-methoxybenzyloxy)-6-methoxy-1H-indole-2-carboxylic acid of formula:

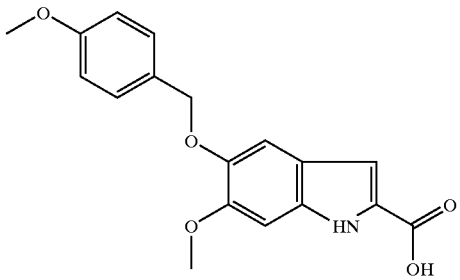

0.2 g of ethyl 6-methoxy-5-(4-methoxybenzyloxy)-1H-indole-2-carboxylate is dissolved in 15 ml of acetone in a reactor. 15 ml of 1N sodium hydroxide are added and the mixture is left to react at room temperature for 6 hours. The solvent is evaporated off under vacuum and the residual aqueous phase is then neutralised by addition of concentrated hydrochloric acid until a pH of 6 is obtained. The solid obtained is filtered off and is taken up in isopropyl ether. The solid is filtered off and dried in a desiccator under vacuum. The recovered mass is 0.05 g, which corresponds to a yield of 30%.

The $^1$H NMR analyses (200 MHz; DMSO), δ in ppm, gave the following results:

3.8 (6H; d), 5.1 (2H; s), 6.9 (4H; m), 7.2 (1H; s), 7.4 (2H; d), 11.6 (1H; s), 12.7 (1H; s).

The structure of the compound obtained is in accordance with the expected structure.

EXAMPLE 6

Synthesis of 5-(4-cyanobenzyloxy)-6-methoxy-1H-indole-2-carboxylic acid:

a) Synthesis of Ethyl 5-(4-cyanobenzyloxy)-6-methoxy-1H-indole-2-carboxylate of formula:

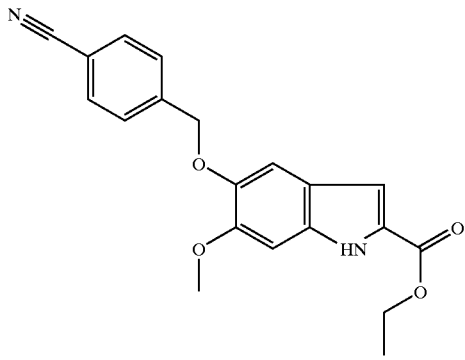

1.6 equivalents of sodium hydride (NaH) and 5 ml of anhydrous dimethylformamide (DMF) are introduced, under argon, into a reactor which has been dried beforehand in an oven. 0.3 g of ethyl 5-hydroxy-6-methoxy-1H-indole-2-carboxylate is then added at 0° C. and the mixture is left to react for 30 minutes at this temperature, in order to form the alkoxide. 1.3 equivalents of 4-cyanobenzyl bromide are then added and the mixture is left to react until it has returned to room temperature, with stirring for 1 h 30. 50 ml of saturated sodium bicarbonate (NaHCO$_3$) solution are then added and this mixture is extracted with twice 50 ml of dichloromethane. The organic phase is dried over sodium sulphate and concentrated to dryness under vacuum, and the residue obtained is purified on a column of silica using dichloromethane as eluent. The recovered mass is 230 mg, which corresponds to a yield of 50%.

b) Synthesis of 5-(4-cyanobenzyloxy)-6-methoxy-1H-indole-2-carboxylic acid of formula:

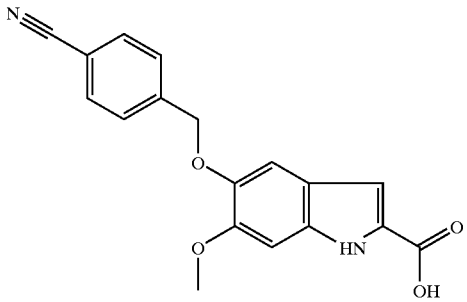

0.230 g of ethyl 5-(4-cyanobenzyloxy)-6-methoxy-1H-indole-2-carboxylate is dissolved in 10 ml of acetone and 5 ml of methanol in a reactor. 10 ml of 1N sodium hydroxide are then added. The reaction is complete in 1 h 30. The solvents are evaporated off under vacuum and the residual aqueous phase is acidified by addition of concentrated hydrochloric acid until a pH of 1 is obtained. The compound obtained is purified by dissolution in ethanol and precipitation from water with stirring. The recovered mass is 0.05 g, which corresponds to a yield of 25%.

The $^1$H NMR analyses (200 MHz; DMSO), δ in ppm, gave the following results:

3.8 (3H; s), 5.1 (2H; s), 7 (3H; t), 7.6 (2H; d), 7.9 (2H; d), 11.7 (1H; s).

The structure of the compound obtained is in accordance with the expected structure.

EXAMPLE 7

Synthesis of 3H-benz[e]indole-2-carboxylic acid:

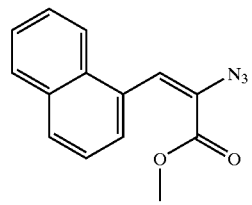

a) Synthesis of Methyl 2-azido-3-naphth-1-ylacrylate of formula:

20 ml of 30% sodium methoxide solution are introduced into a reactor. The system is cooled to 0° C. and 5 g of naphthaldehyde are then added slowly under argon. 8.3 g of ethyl azidoacetate, diluted in 10 ml of methanol, are then added dropwise. The mixture is left to react for 5 hours at 0° C. 50 ml of water are added to the reaction and this mixture is extracted with 2×30 ml of dichloromethane. The organic phase is dried over sodium sulphate and evaporated to dryness under vacuum, and the product obtained is purified on a column of silica using dichloromethane as eluent. The recovered mass is 4 g, which corresponds to a yield of 70%.

b) Synthesis of Methyl 3H-benz[e]indole-2-carboxylate of formula:

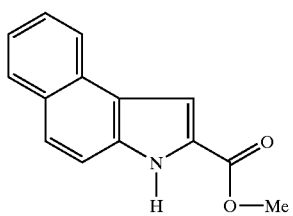

3 g of methyl 2-azido-3-naphth-1-ylacrylate are dissolved in 20 ml of toluene in a reactor. The mixture is refluxed for 3 hours. The solvent is evaporated off under vacuum and the residue is then taken up in 20 ml of hot heptane. A solid which precipitates is obtained. The solid is filtered off and dried in a desiccator under vacuum. The recovered mass is 3.1 g, which corresponds to a yield of 89%.

c) Synthesis of 3H-benz[e]indole-2-carboxylic acid of formula:

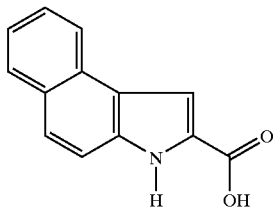

1 g of methyl 3H-benz[e]indole-2-carboxylate is dissolved in 10 ml of methanol and 20 ml of acetone in a reactor. 50 ml of 1N sodium hydroxide are then added. This mixture is left to react for 1 h 30 at room temperature. The solvents are evaporated off under vacuum and the residual aqueous phase is acidified by adding concentrated hydrochloric acid until a pH of 1 is obtained. The solid is filtered off and is recrystallized from a water/ethanol mixture. The recovered mass is 0.5 g, which corresponds to a yield of 53%.

The $^1$H NMR analyses (200 MHz; DMSO), δ in ppm, gave the following results:

7.75 (5H; m), 8.1 (1H; d), 8.5 (1H; d), 12.3 (1H; s), 13.1 (1H; s).

|  | Elemental analysis | | | |
| --- | --- | --- | --- | --- |
|  | C in % | H in % | N in % | O in % |
| Theory | 73.92 | 4.29 | 6.63 | 15.15 |
| Found | 73.58 | 4.23 | 6.52 | 15.15 |

EXAMPLE 8

Synthesis of 3-methyl-3H-benz[e]indole-2-carboxylic Acid:

a) Synthesis of Methyl 3-methyl-3H-benz[e]indole-2-carboxylate of formula:

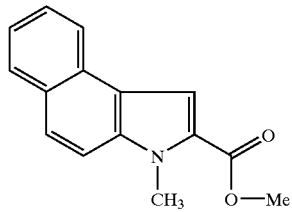

1.1 equivalents of sodium hydride (NaH) and 5 ml of anhydrous dimethylformamide (DMF) are introduced, under argon, into a reactor. 0.1 g of methyl 3H-benz[e]indole-2-carboxylate is added and the mixture is left stirring until a homogeneous medium is obtained. 0.1 ml of methyl iodide is then added and the mixture is left to react at room temperature. The reaction is complete in 30 minutes. 30 ml of saturated NaCl solution are then added and the mixture is then extracted with twice 50 ml of dichloromethane. The organic phase is concentrated to dryness under vacuum. The recovered mass is 0.11 g, which corresponds to a yield of 100%.

b) Synthesis of 3-methyl-3H-benz[e]indole-2-carboxylic acid of formula:

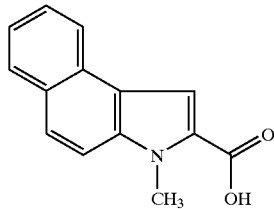

0.1 g of methyl 3-methyl-3H-benz[e]indole-2-carboxylate is dissolved in 7 ml of acetone in a reactor. 10 ml of 1N sodium hydroxide are then added. The mixture is left to react at room temperature for 1 hour. The solvent is evaporated off under vacuum and the residual aqueous phase is neutralised by bringing the pH to 6 by addition of concentrated hydrochloric acid. The solid obtained is washed several times with water.

The recovered mass is 0.057 g, which corresponds to a yield of 61%.

The $^1$H NMR analyses (200 MHz; DMSO), δ in ppm, gave the following results:

7.35 (2H; m), 7.7 (4H; m), 8.2 (1H; d), 12.7 (1H; s).

EXAMPLE 9

Synthesis of 1-[3,5-bis(trifluoromethyl)benzyl]-5-[3,5-bis(trifluoromethyl)benzyloxy]-6-methoxy-1H-indole-2-carboxylic acid:

a) Synthesis of Ethyl 1-[3,5-bis(trifluoromethyl)benzyl]-5-[3,5-bis(trifluoromethyl)benzyloxy]-6-methoxy-1H-indole-2-carboxylate of formula:

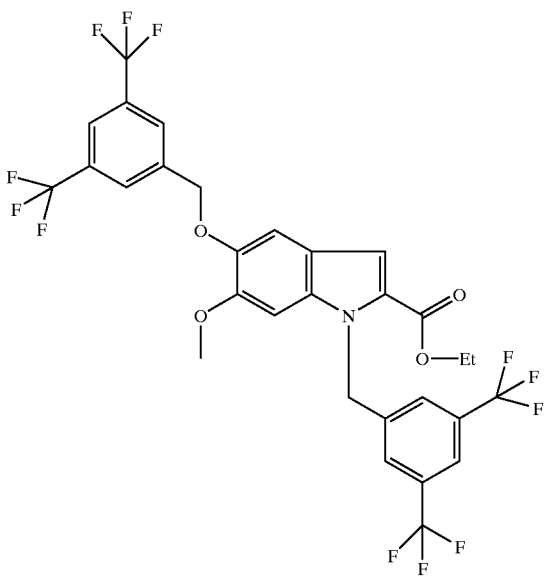

1.6 equivalents of sodium hydride (NaH) and 5 ml of anhydrous dimethylformamide (DMF) are introduced, under argon, into a reactor which has been dried beforehand in an oven. 0.3 g of ethyl 5-hydroxy-6-methoxy-1H-indole-2-carboxylate is then added at +3° C. and the mixture is left to react for 30 minutes at this temperature in order to form the alkoxide. 1.4 equivalents of 3,5-bis(trifluoromethyl)benzyl bromide are then added and this mixture is left to react at this temperature for 1 h 30. 50 ml of saturated sodium bicarbonate ($NaHCO_3$) solution are then added and this mixture is extracted with twice 50 ml of dichloromethane. The organic phase is dried over sodium sulphate and concentrated to dryness under vacuum, and the residue obtained is purified on a column of silica using dichloromethane as eluent. The recovered mass is 200 mg, which corresponds to a yield of 40%.

b) Synthesis of 1-[3,5-bis(trifluoromethyl)benzyl]-5-[3,5-bis(trifluoromethyl)benzyloxy]-6-methoxy-1H-indole-2-carboxylic acid of formula:

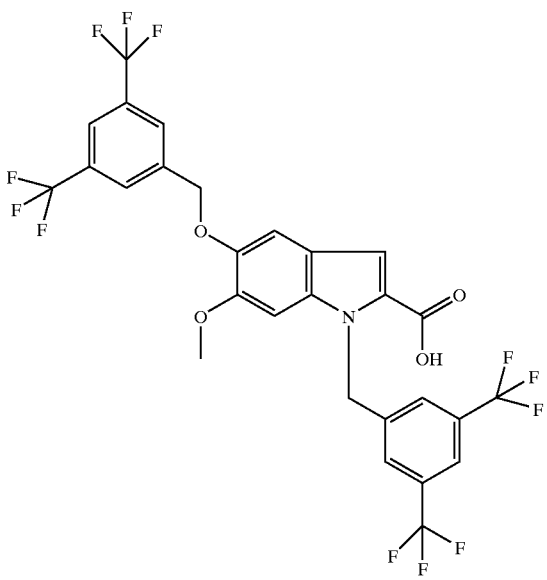

0.2 g of ethyl 1-[3,5-bis(trifluoromethyl)benzyl]-5-[3,5-bis(trifluoromethyl)benzyloxy]-6-methoxy-1H-indole-2-carboxylate is dissolved in 10 ml of acetone and 5 ml of methanol in a reactor. 10 ml of 1N sodium hydroxide are then added. The mixture is left to react for 2 hours at room temperature. The solvents are evaporated off under vacuum and the residual aqueous phase is acidified by addition of concentrated hydrochloric acid until a pH of 3 is obtained. This mixture is purified by taking it up in isopropyl ether. The recovered mass is 0.08 g, which corresponds to a yield of 45%.

The $^1H$ NMR analyses (200 MHz; DMSO), δ in ppm, gave the following results:

3.8 (3H; s), 5.3 (2H; s), 6.2 (2H; s), 7.2 (3H; t), 8.0 (6H; m).

The structure of the compound obtained is in accordance with the expected structure.

EXAMPLE 10

Evaluation of the Inhibitory Effect of Compounds of the Invention on Type 1 and Type 2 5α-Reductases:

The coding sequences (complementary deoxyribonucleic acids: cDNA) of 5α-reductase 1 and of 5α-reductase 2 were cloned in the eukaryotic expression vector pSG5 (Stratagene). The enzymes were over-expressed after transient transfection of COS7 cells (ATCC, CRL 1651). The cDNAs of 5α-reductase 1 and of 5α-reductase 2 were obtained by reverse transcription and polymerase chain reaction (PCR) using specific primers, starting with total RNA from human testicles (sold by the company Clontech).

The primers used to obtain the 5α-reductase 1 cDNA are:

+ strand: 5' CCCAGCCCTGGCGATGGCAAC 3',

− strand: 5' GGATATTCAACCTCCATTTCAG 3'.

The primers used to obtain the 5α-reductase 2 cDNA are:

+ strand: 5' GCGATGCAGGTTCAGTG 3'

− strand: 5' ATTGTGGGAGCTCTGCT 3'.

By standard genetic engineering techniques, the 5α-reductase 1 cDNA obtained was inserted into the BamHI site of pSG5 and that of 5α-reductase 2 was inserted into the EcoRI site (see Maniatis et al., Molecular Cloning, Cold Spring Harbor, 1989).

The positive clones (recombinants) were identified by the hybridization technique with a cold probe (Plex luminescent kits, Millipore) and mapped by enzymatic digestions and partial sequencing.

After transient transfection, the COS7 cells are lysed in a 10 mM Tris-HCl, pH=7/150 mM KCl/1 mM EDTA buffer by 3 cycles of freezing/thawing. The homogenate is centrifuged at 100,000× g for 1 hour. The pellets containing the 5α-reductase 1 or the 5α-reductase 2 are taken up in a 40 mM, pH 6.5 phosphate buffer or a 40 mM, pH 5.5 citrate buffer for the 5α-reductase 1 or 5α-reductase 2, respectively.

5 µg of proteins thus obtained are incubated in a well of a 96-well plate (NUNC) in the presence of 1 nM $^{14}C$-testosterone (Amersham) and 5 mM nicotinamide adenosine dinucleotide phosphate, reduced form (NADPH) (Sigma) in the corresponding buffer (40 mM, pH 6.5 phosphate buffer or 40 mM, pH 5.5 citrate buffer for the 5α-reductase 1 or 5α-reductase 2, respectively) for 50 minutes at 37° C. after addition of the test products. The test products are added at concentrations of $10^{-4}$ M to $10^{-10}$ M, diluted in 40 mM, pH 6.5 phosphate buffer or 40 mM, pH 5.5 citrate buffer for the 5α-reductase 1 or 5α-reductase 2, respectively.

The reaction mixtures are then placed directly on a silica plate (HPTLC, 60F 254, Merck) and subjected to chromatography (solvent=10% diethyl ether, 90% dichloromethane). They are then analysed by digital autoradiography (Berthold).

The inhibition of the activity of the isoenzymes is measured by calculating the percentage of dihydrotestosterone formed from $^{14}C$-testosterone relative to an untreated control.

The results are given in the table below:

| | | | | | | 5α-reductases: $IC_{50}$ | |
|---|---|---|---|---|---|---|---|
| Ex. | X | Y | Z | $R_1$ | $R_2$ | Type I (μM) | Type II (nM) |
| 1 | OCH$_2$Ph | H | —OMe | H | H | 1–4 | >100,000 |
| 2 | OCH$_2$Ph—(CF$_3$)$_2$ | H | —OMe | H | H | 10 | >100,000 |
| 3 | H | OCH$_2$Ph—(CF$_3$)$_2$ | —OMe | H | H | 0.5 | 1–5 |
| 4 | H | OCH$_2$Ph—(OMe)$_3$ | —OMe | H | H | >100 | 10 |
| 5 | H | OCH$_2$Ph—(OMe) | —OMe | H | H | 1–5 | 10 |
| 6 | H | OCH$_2$Ph(CN) | —OMe | H | H | 5 | 40 |
| 7 | | Ph | H | H | H | 3 | 6000 |
| 8 | | Ph | H | H | Me | 0.5 | 10,000 |
| a | H | OCH$_2$Ph | —OMe | H | H | 1 | 1 |
| b | H | OCH$_2$Ph | —OCH$_2$Ph | Me | H | >100 | 1000 |
| c | H | OCH$_2$Ph | —OCH$_2$Ph | H | H | >100 | 5 |

Ph = —C$_6$H$_5$; Me = —CH$_3$
a,b,c: compounds whose synthesis has not been given in the examples.

The compounds of Examples 1 and 2 have very pronounced specificity with respect to type 1 5α-reductase.

The compounds of Examples 7 and 8 have pronounced specificity with respect to type 1 5α-reductase.

The compounds of Examples 3, 5 and 6 and compound a are very good inhibitors of the two types of 5α-reductase.

The compound of Example 4 and compound c have more pronounced specificity for the type 2 5α-reductase.

Compound b is a moderate inhibitor with more pronounced specificity for the type 1 5α-reductase.

EXAMPLE 11

Examples of Compositions Containing an Indolecarboxylic Derivative.

These compositions are obtained by the usual techniques commonly used in cosmetics or in pharmacy.

| Niosomal gel: | | |
|---|---|---|
| Chimexane NS ® | | 1.800 g |
| Monosodium stearoylglutamate | | 0.200 g |
| Compound of Example 1 | | 1.000 g |
| Carbomer | | 0.200 g |
| Triethanolamine | q.s. | pH = 7 |
| Preserving agents | q.s. | |
| Fragrances | q.s. | |
| Demineralized water | q.s. | 100.000 g |

This gel is applied to the scalp once or twice daily.

| Lotion for preventing hair loss: | |
|---|---|
| Compound of Example 3 | 2.000 g |
| Propylene glycol | 30.000 g |

| -continued | | |
|---|---|---|
| Lotion for preventing hair loss: | | |
| Ethyl alcohol | | 40.500 g |
| Water | q.s. | 100.000 g |

This lotion is applied to the scalp once or twice daily at a rate of 1 ml per application.

| Thickened lotion for preventing hair loss: | | |
|---|---|---|
| Compound of Example 7 | | 5.000 g |
| Kawain | | 2.000 g |
| Hydroxypropylcellulose (Klucel G from the company Hercules) | | 3.500 g |
| Ethyl alcohol | q.s. | 100.000 g |

This thickened lotion is applied to the scalp once or twice daily at a rate of 1 ml per application.

| Niosomal lotion: | | |
|---|---|---|
| Chimexane NL ® | | 0.475 g |
| Cholesterol | | 0.475 g |
| Monosodium stearoylglutamate | | 0.050 g |
| Compound of Example 8 | | 2.000 g |
| Preserving agents | q.s. | |
| Dyes | q.s. | |
| Fragrance | q.s. | |
| Demineralized water | q.s. | 100.000 g |

This lotion is applied to the scalp once or twice daily at a rate of 1 ml per application.

| Lotion for preventing hair loss: | |
| --- | --- |
| Compound of Example 3 | 2.500 g |
| Propylene glycol monomethyl ether (Dowanol PM from Dow Chemical) | 20.000 g |
| Hydroxypropylcellulose (Klucel G from Hercules) | 3.000 g |
| Ethanol | 40.000 g |
| Minoxidil | 2.000 g |
| Water q.s. | 100.000 g |

This thickened lotion is applied to the scalp once or twice daily at a rate of 1 ml per application.

| Lotion for preventing hair loss: | | |
| --- | --- | --- |
| Compound of Example 7 | | 0.200 g |
| Propylene glycol | | 10.000 g |
| Isopropyl alcohol | q.s. | 100.000 g |

1 ml of this lotion is applied to the scalp at a frequency of once or twice daily.

With each of the compositions described in the above examples, after treatment for several months and depending on the individual treated, a slowing-down of the hair loss and/or a regrowth effect were found.

What is claimed is:

1. A method for the treatment of disorders associated with overactivity of type II 5α-reductase comprising administering to a patient in need of such treatment an effective amount of at least one compound corresponding to the formula (I)

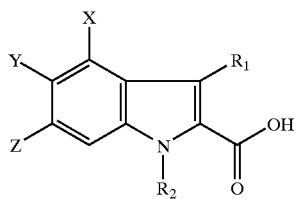

Formula (I)

in which
  Y represents a hydrogen atom or a radical —OCHR$_3$R$_4$, in which R$_3$ is a hydrogen atom or an optionally substituted phenyl radical or alternatively a 5- or 6-membered heterocycle and R$_4$ is an optionally substituted phenyl radical or alternatively a 5- or 6-membered heterocycle, or R$_3$ and R$_4$ taken together form, with the carbon atom, a 5- or 6-membered ring or heterocycle;
  X represents a hydrogen atom;
  Z represents a hydrogen atom or a radical —OR$_5$ in which R$_5$ is a C$_1$–C$_6$ alkyl radical or a C$_6$–C$_{12}$ aralkyl radical;
  R$_1$ represents a hydrogen atom or a C$_1$–C$_6$ alkyl radical or a C$_6$–C$_{12}$ aralkyl radical which is optionally substituted;
  R$^2$ represents a hydrogen atom or a C$_1$–C$_6$ alkyl radical or a radical —CHR$_3$R$_4$, in which R$_3$ and R$_4$ have the above definitions.

2. The method of claim 1, wherein the compound is:
5-[3,5-bis(trifluoromethyl)benzyloxy]-6-methoxy-1H-indole-2-carboxylic acid,
5-(3,4,5-trimethoxy-benzyloxy)-6-methoxy-1H-indole-2-carboxylic acid,
5-(4-methoxybenzyloxy)-6-methoxy-1H-indole-2-carboxylic acid,
5-(4-cyanobenzyloxy)-6-methoxy-1H-indole-2-carboxylic acid,
1-(3,5-bis-trifluoromethyl-benzyl)-5-(3,5-trifluoromethyl-benzyloxy)-6-methoxy-1H-indole-2-carboxylic acid,
a compound of claim 1 wherein Y is —OCH$_2$Ph, Z is —OMe, R$_1$ and R$_2$ are hydrogen atoms,
a compound of claim 1 wherein Y and Z are —OCH$_2$Ph, R$_1$ is —Me, and R$_2$ is a hydrogen atom,
or a compound of claim 1 wherein Y and Z are —OCH$_2$Ph, and R$_1$ and R$_2$ are hydrogen atoms.

3. The method of claim 1, wherein the disorder associated with overactivity of type II 5α-reductase is an androgen-associated disorder.

4. The method of claim 3, wherein the androgen-associated disorder is acne, hirsutism, seborrhoea, androgenic alopecia, prostate carcinoma, or benign hyperplasia of the prostate.

5. The method of claim 3, wherein the androgen-associated disorder is hyperseborrhoea or acne.

6. The method of claim 1, wherein the compound is used in an amount representing from 0.001% to 10% of the total weight of the composition.

7. The method of claim 5, wherein in that the compound is used in an amount representing from 0.01% to 5% of the total weight of the composition.

8. An indolecarboxylic derivative having formula (I'):

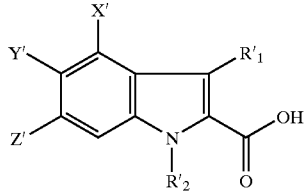

Formula (I')

in which
  Y' represents a hydrogen atom or a radical —OCHR$_{13}$R$_{14}$, in which R$_{13}$ is a hydrogen atom or an optionally substituted phenyl radical or alternatively a 5- or 6-membered heterocycle and R$_{14}$ is an optionally substituted phenyl radical or alternatively a 5- or 6-membered heterocycle, or R$_{13}$ and R$_{14}$ taken together form, with the carbon atom, a 5- or 6-membered ring or heterocycle;
  X' represents a hydrogen atom;
  Z represents a hydrogen atom or a radical —OR'$_5$ in which R$_5$ is a C$_1$–C$_6$, alkyl radical or a C$_6$–C$_{12}$, aralkyl radical;
  R'$_1$ represents a hydrogen atom or a C$_1$–C$_6$, alkyl radical or a C$_6$–C$_{12}$ aralkyl radical, which is optionally substituted;
  R'$_2$ represents a hydrogen atom or a C$_1$–C$_6$ alkyl radical or a radical —CHR'$_3$R'$_4$ in which R'$_3$ and R'$_4$ have the above definitions;
  or the esters thereof or the optical isomers thereof, alone or as a mixture in all proportions, the acylated forms thereof or alternatively the pharmaceutically acceptable salts thereof.

9. The derivative compound of claim 8, wherein R'$_1$ is an optionally substituted C$_1$–C$_6$ alkyl radical.

10. The derivative compound of claim 8, wherein R'$_1$ is an optionally substituted C$_6$–C$_{12}$ aralkyl radical.

11. The derivative compound of claim 8, wherein $R'_2$ is a $C_1$–$C_6$ alkyl radical.

12. The derivative compound of claim 8, wherein, when $R'_3$ or $R'_4$ independently of each other is an optionally substituted phenyl radical, the radical is substituted with a cyano group, a trifluoromethyl group, a methoxy radical or a halogen atom.

13. The derivative compound of claim 8, wherein, when $R'_3$ or $R'_4$ independently of each other, is a heterocycle, this heterocycle comprises pyridine, quinoline, imidazole, benzimidazole, tetrahydrofuran or furan.

14. The derivative compound of claim 8, wherein $R'_5$ is a $C_1$–$C_6$ alkyl radical.

15. The derivative compound of claim 8, wherein $R'_5$ is a $C_6$–$C_{12}$ aralkyl radical.

16. The derivative compound of claim 8, wherein the compound is:

5-[3,5-bis(trifluoromethyl)benzyloxy]-6-methoxy-1H-indole-2-carboxylic acid, 5-(3,4,5-trimethoxy-benzyloxy)-6-methoxy-1H-indole-2-carboxylic acid, 5-(4-methoxybenzyloxy)-6-methoxy-1H-indole-2-carboxylic acid, 5-(4-cyanobenzyloxy)-6-methoxy-1H-indole-2-carboxylic acid, 1-(3,5-bis-trifluoromethyl-benzyl)-5-(3,5-trifluoromethyl-benzyloxy)-6-methoxy-1H-indole-2-carboxylic acid, a compound of claim 1 wherein Y is —OCH$_2$Ph, Z is —OMe, $R_1$ and $R_2$ are hydrogen atoms, a compound of claim 1 wherein Y and Z are —OCH$_2$Ph, $R_1$ is —Me, and $R_2$ is a hydrogen atom, or a compound of claim 1 wherein Y and Z are —OCH$_2$Ph and $R_1$ and $R_2$ are hydrogen atoms.

17. A composition comprising a pharmaceutically or cosmetically effective amount of at least one compound of formula (I') of claim 8 and a pharmaceutically or cosmetically acceptable carrier therefor.

18. The composition of claim 17, comprising at least one compound of formula (I') in an amount representing from 0.001% to 10% of the total weight of the composition.

19. The composition of claim 17, further comprising at least one agent selected from the group consisting of antibacterial agents, antiparasitic agents, antifungal agents, antiviral agents, anti-inflammatory agents, anti-pruriginous agents, anaesthetics, keratolytic agents, anti-free-radical agents, anti-seborrhoeic agents, antidandruff agents, anti-acne agents, agents for reducing skin differentiation and/or proliferation and/or pigmentation, and extracts of plant or bacterial origin.

20. A method for treating disorders associated with overactivity of type II 5α-reductase comprising administering the composition of claim 17 to a patient in need of such treatment.

21. A method for treating androgen-dependent disorders comprising administering the composition of claim 17 to a patient in need of such treatment.

22. A method for treating seborrhea, acne, hirsutism, androgenic alopecia, prostate carcinoma, and/or benign hyperplasia of the prostate comprising administering the composition of claim 17 to a patient in need of such treatment.

23. A method for treating the skin, hair and/or scalp comprising applying to a patient in need of such treatment a therapeutically effective amount of the composition of claim 17 to stimulate hair growth and/or slow down hair loss.

* * * * *